US011439781B2

(12) United States Patent
Schwaibold (10) Patent No.: US 11,439,781 B2
(45) Date of Patent: *Sep. 13, 2022

(54) BREATHING DEVICE AND METHOD FOR CONTROLLING A RESPIRATORY GAS SOURCE

(71) Applicant: Loewenstein Medical Technology S.A., Luxembourg (LU)

(72) Inventor: Matthias Schwaibold, Karlsruhe (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 102 days.

This patent is subject to a terminal disclaimer.

(21) Appl. No.: 16/714,927

(22) Filed: Dec. 16, 2019

(65) Prior Publication Data

US 2020/0114101 A1  Apr. 16, 2020

Related U.S. Application Data

(63) Continuation of application No. 14/842,053, filed on Sep. 1, 2015, now Pat. No. 10,512,742.

(30) Foreign Application Priority Data

Sep. 5, 2014  (DE) .......................... 102014012907.1
Sep. 15, 2014  (DE) .......................... 102014011951.3

(51) Int. Cl.
*A61M 16/00* (2006.01)
*A61M 16/06* (2006.01)
(52) U.S. Cl.
CPC ........ *A61M 16/0069* (2014.02); *A61M 16/00* (2013.01); *A61M 16/0051* (2013.01);
(Continued)

(58) Field of Classification Search
CPC .............. A61M 16/00; A61M 16/0051; A61M 16/006; A61M 16/0069; A61M 16/0072;
(Continued)

(56) References Cited

U.S. PATENT DOCUMENTS 5,797,393 A * 8/1998 Kohl ................... A61M 16/205
128/204.23
5,931,162 A   8/1999 Christian
(Continued)

FOREIGN PATENT DOCUMENTS

DE      19516536 A1    8/1998
DE    102006048680 B3   9/2007
WO      2013120690 A1   8/2013

*Primary Examiner* — Jennifer Robertson
(74) *Attorney, Agent, or Firm* — Abel Schillinger, LLP (57) ABSTRACT

A breathing device comprises a respiratory gas source for generating a gas pressure for a patient, delivered by a respiratory mask, a measuring unit for measuring a measurement quantity characteristic of inhalation or exhalation, and a control unit which determines the patient's tidal volume from the measurement quantity and compares this with a setpoint value of the tidal volume. The control unit regulates the respiratory gas source such that the generated gas pressure is made available until the setpoint value of the tidal volume is reached. In addition, further regulation of a parameter characteristic of the patient's breathing is carried out. The method for controlling a respiratory gas source with a control unit for a patient's breathing comprises regulation of the patient's tidal volume by providing and applying inspiratory pressure and simultaneous regulation of a further breathing parameter.

20 Claims, 8 Drawing Sheets

(52) U.S. Cl.
CPC ......... *A61M 16/06* (2013.01); *A61M 2205/18* (2013.01); *A61M 2205/3334* (2013.01); *A61M 2205/502* (2013.01)

(58) Field of Classification Search
CPC ........ A61M 16/022–026; A61M 16/06; A61M 2205/18; A61M 2205/3334; A61M 2205/502
See application file for complete search history.

(56) References Cited

U.S. PATENT DOCUMENTS

| | | | |
|---|---|---|---|
| 10,512,742 B2* | 12/2019 | Schwaibold | A61M 16/024 |
| 2008/0020525 A1 | 1/2008 | Krueger et al. | |
| 2011/0226248 A1* | 9/2011 | Duff | A61M 16/0051 128/204.23 |
| 2012/0315614 A1* | 12/2012 | Krauza | A61M 16/024 434/247 |
| 2014/0311491 A1* | 10/2014 | Klein | A61B 5/083 128/204.22 |
| 2015/0335839 A1* | 11/2015 | Mersmann | A61M 16/0003 128/202.22 |

* cited by examiner

BREATHING DEVICE AND METHOD FOR CONTROLLING A RESPIRATORY GAS SOURCE

CROSS-REFERENCE TO RELATED APPLICATIONS

The present application is a continuation of U.S. patent application Ser. No. 14/842,053, filed Sep. 1, 2015, which claims priority under 35 U.S.C. § 119 of German Patent Applications Nos. 10 2014 012 907.1, filed Sep. 5, 2014, and 10 2014 011 951.3, filed Sep. 15, 2014. The entire disclosures of the aforementioned applications are expressly incorporated by reference herein.

BACKGROUND OF THE INVENTION

1. Field of the Invention

The present invention relates to a method for controlling a respiratory gas source with a control unit, and to a breathing device.

2. Discussion of Background Information

Sleep disorders are generally due to obstructive sleep apnea (OSA), in which the respiratory flow is temporarily either significantly reduced (hypopnea) or fully interrupted (apnea). This oxygen deficit, however, is detrimental to restful sleep. Stress situations occur, which in the long and medium term can damage the heart. For this reason, patients with obstructive sleep apnea are additionally ventilated by sleep therapy devices or home breathing devices.

For the treatment of sleep apnea, there are different devices which can implement various therapies. One standard therapy is CPAP (continuous positive airway pressure) therapy, in which the breathing device applies a pressure elevated relative to atmospheric pressure to the patient. The patient breathes by himself. The device thus only assists spontaneous respiration, the airways being opened by the continuous pressure.

A further therapy is APAP (automated positive airway pressure) therapy. In this case, the pressure is provided only during a respiratory problem (apnea or hypopnea). As an alternative, patients with periodic respiration or central apnea have to date been treated with devices which offer two different pressure levels, so-called bilevel devices. These devices provide two pressure levels, a higher inspiratory pressure (IPAP) and a lower expiratory pressure (EPAP). The pressure is provided only during periods which exhibit reduced or no spontaneous respiration. This way, the occurrence of oxygen saturation or arousal is prevented. If the patients are suffering from Cheyne-Stokes respiration, in which there is a periodic increase and decrease of the respiratory depth and of the spacing of the individual respiratory cycles, adaptive servoventilation is carried out as a form of therapy, in which the respiratory pressure is automatically regulated anticyclically in each respiratory cycle in order to induce stabilization of the respiration by variable pressure assistance.

These forms of therapy based on pressure monitoring contrast with volume-monitored therapy. In the case of volume compensation, a setpoint volume or target volume is specified, which the patient should reach so that he is ventilated sufficiently. The device respectively measures the patient's respiratory volume and increases the pressure to be administered, generally the inspiratory pressure, if the target volume is fallen below. Typical adjustment possibilities for such devices are the target volume, an interval for the inspiratory pressure and the regulation rate.

In view of the foregoing, it would be advantageous to have available an improved breathing device and a method for controlling a respiratory gas source, which ensures comfortable and robust breathing of a patient even in the event of complex illnesses.

SUMMARY OF THE INVENTION

The present invention provides a method for controlling a respiratory gas source comprising a control unit for a patient's breathing. The method comprises regulating the patient's tidal volume by providing and applying inspiratory pressure and simultaneously regulating a further breathing parameter.

In one aspect of the method, the regulation of the tidal volume may comprise:
measuring the gas flow, the volume flow or an equivalent respiratory gas quantity,
determining the air volume received by the patient,
establishing a setpoint value of the patient's tidal volume,
generating an inspiratory pressure,
regulating the inspiratory pressure in such a way that the setpoint value of the tidal volume is reached.

In another aspect of the method, the regulation of the further breathing parameter may comprise at least one of the following:
regulation of an automatic trigger for detecting exhalation and/or inhalation,
automatic adaptation of the exhalation pressure,
automatic regulation of the respiratory frequency,
anticyclic pressure reaction regulation,
regulation of the transition pressure between inspiratory pressure and expiratory pressure.

In yet another aspect of the method, the expiratory pressure which is less than an inspiratory pressure may be generated, so that a pressure difference is formed. For example, the pressure difference may be regulated until the tidal volume received by the patient is equal to the setpoint value of the tidal volume.

In a still further aspect, the inspiratory pressure may be variable between a lower inspiratory pressure limit and an upper inspiratory pressure limit, and the expiratory pressure may be variable between a lower expiratory pressure limit and an upper expiratory pressure limit.

In another aspect of the method of the present invention, the regulation of the tidal volume may be carried out over one or more respiratory cycles of the patient, the mandatory ventilation being adapted to an existing spontaneous respiration of the patient.

In another aspect of the method, the inhalation and exhalation may be detected by the control unit by cyclic measurement and evaluation of a respiratory parameter, and the instantaneous tidal volume may be measured and compared with a setpoint value of the tidal volume, and the inspiratory pressure or the pressure difference between inspiratory pressure and the expiratory pressure may be increased if the setpoint value is fallen below.

In another aspect of the method, the expiratory pressure may be adapted automatically with the aid of a predetermined therapeutic aim.

In another aspect of the method, in the event of additional regulation of the respiratory frequency and mandatory ventilation, automatic regulation of the respiratory frequency may be carried out as a function of a patient's spontaneous frequency. For example, automatic regulation of the respiratory frequency may be variable as a fixed percentage of the spontaneous respiratory frequency, as a fixed difference from the spontaneous respiratory frequency or iteratively in order to generate accelerated or retarded spontaneous respiration.

In another aspect of the method, a setpoint value of the tidal volume may be stored as a lower limit value and, in the event of a tidal volume above the limit value, an additional anticyclic pressure reaction may be carried out in order to counteract a variation of the tidal volume.

In another aspect of the method, the applied pressure difference between the inspiratory pressure and the expiratory pressure may be varied as a function of the volume difference between the currently measured tidal volume and the setpoint value of the tidal volume. For example, an adaptive adaptation is carried out, e.g., with a predetermined ramp time after which the setpoint value is reached and the pressure difference has reached its maximum, or with a predetermined fraction of inspiration and/or expiration or by regulation with a predetermined pressure profile.

In another aspect of the method of the present invention, the patient's dead space volume may be taken into account in determining the tidal volume.

The present invention also provides a breathing device. The device comprises a respiratory gas source for generating a gas pressure for a patient, which is delivered by a respiratory mask, a measuring unit for measuring a measurement quantity characteristic of inhalation or exhalation, and a control unit which determines the patient's tidal volume from the measurement quantity, compares this with a setpoint value of the tidal volume and regulates the respiratory gas source in such a way that the generated gas pressure is made available until the setpoint value of the tidal volume is reached. In addition, further regulation of a breathing parameter characteristic of the patient's breathing is carried out and a corresponding regulating signal is delivered to the respiratory gas source.

In one aspect of the device, the control unit may be formed and configured in order to carry out the method of the present invention as set forth above (including the various aspects thereof).

In another aspect of the device, the device may comprise
an alarm unit for emitting an alarm signal, preferably an audible signal, the alarm unit preferably being a loudspeaker or a buzzer,
a visualization unit, preferably a display, for displaying parameters and/or breathing parameters and/or measurement values and/or values further processed from measurement values, or transmitting them to an external visualization device via an interface for display,
a memory unit for storing measured values, characteristic breathing parameters, alarms, respiratory volumes or adjustment parameters,
a computation unit for statistical evaluation, and
an operating unit which comprises one or more man/machine interfaces and preferably has a touchscreen display.

In the scope of the invention, it has been found that therapy with volume compensation is a suitable treatment of patients with sleep disorders which are due to hypopnea. The volume compensation ensures that the patients are ventilated sufficiently and a sufficiently large respiratory volume is provided. In this way, desired oxygen saturations are reliably achieved. Patients find such therapy comfortable and the sleep as restful.

It has furthermore been found that devices for volume compensation and for providing a setpoint value for a tidal volume (respiratory volume) generally provide only few, fixed adjustment possibilities as explained above. Furthermore, other devices are known which use other established regulating algorithms, for example automatic bilevel pressure application or anticyclic servoventilation. These are highly suitable for other therapies, for example for obstructions of the airways or Cheyne-Stokes disorder.

In the scope of the invention, it has been discovered that a combination of target volume regulation, i.e. regulation of the patient's tidal volume, and regulation of a further breathing parameter characteristic of the patient's breathing has great advantages. Regulation of a breathing parameter characteristic of breathing is intended, for example, to mean automatic inhalation pressure regulation which detects exhalation and/or inhalation. Further regulation is automatic adaptation of the exhalation pressure, in which case the pressure adaptation may take place both up and down. The aim is in this case to treat obstructions of the airways.

Further regulations, which may be combined with the regulation of tidal volume according to the invention, are automatic adjustment of the respiratory frequency, regulation of the anticyclic pressure reaction (anticyclic servoventilation) or regulation of the transition pressure between the inspiratory and expiratory pressures.

It is of course also possible, besides regulation of the tidal volume, to combine a number of the other regulations, so that not only the tidal volume but also an automatic respiratory frequency is regulated, and in addition, for example, automatic adaptation of the exhalation pressure or anticyclic servoventilation is carried out. In this case, at the same time, arbitrary combinations of the given and known regulations with the regulation of the tidal volume may be envisioned. Regulation of the tidal volume and a further breathing parameter at the same time does not mean simultaneous regulation, but only the possibility of regulating the two quantities together in order to ensure maximally efficient and robust breathing which is comfortable and reliable for the patient. The regulation may be carried out with a time offset, overlapping in time or simultaneously. The breathing device provides at least two regulating possibilities in one or more control units, although the tidal volume is in any event regulated.

For the regulation, the tidal volume is either observed, measured and regulated for each respiratory cycle, or per minute or over a plurality of respiratory cycles, so that the tidal volume is to be adjusted only after a predefined number of respiratory cycles. To this end, the average over the predetermined number of respiratory cycles is generally considered and evaluated. The averaging is preferably a weighted averaging.

The regulation of the tidal volume is carried out by first measuring the gas flow, the volume flow or an equivalent respiratory gas quantity. The air volume received by the patient is determined from this measurement quantity. A predefined setpoint value of the tidal volume is used as a regulating quantity. The setpoint value (setpoint tidal volume, also referred to as the target volume) is generally indicated in milliliters. Its adjustment may be carried out by the patient himself. The value of the target volume may be calculated or estimated by the device using individual parameters, for example from the age, the weight and the size of the patient or from similar values. Lastly, it is also possible to determine this value by measurements, for example during a monitoring phase by a doctor.

As a function of the determined air volume of the patient and the target volume (setpoint tidal volume), the regulation of the inspiratory pressure is carried out in such a way that the setpoint value of the tidal volume is reached. In this case, regulation is possible already after measurement of the air volume during a respiratory cycle, or over a longer period of time which comprises a plurality of respiratory cycles of the patient. Either a predetermined number of respiratory cycles may be observed and measured, or the patient's respiratory minute volume is determined. In this case, regulation of the respiratory minute volume is carried out in comparison with a minute-referenced setpoint tidal volume. Of course, longer or shorter periods of time may also be used as a basis for the regulation by corresponding specification on the breathing device and by corresponding control.

Although a target tidal volume is not taken into account in the previously known automatic modes and regulations of the known devices, for example auto-bilevel regulation or regulation of the anticyclic servoventilation, the advantages of the various technologies are expediently combined according to the invention in order to achieve therapeutic successes.

One application example which may be mentioned is obesity hypoventilation syndrome (OHS), in which a constriction of the airways occurs because of their own body mass or extreme obesity. Obstructions of the upper airways and hypoventilation often occur together only in the supine position. If the patient is on their side, the therapy pressures which are administered to the patient can be significantly reduced. This leads to an increase in the comfort and a reduction in the side effects. Only when the patient turns onto his back is the expiratory pressure (EPAP) also automatically increased, since the breathing device itself detects the obstructions. Furthermore, in the supine position, because of the obstructions occurring, the minimum respiratory volume is no longer reached so that a lack of oxygen saturation occurs in the patient. In order to achieve the lacking minimum respiratory volume (which corresponds to the adjusted setpoint value of the tidal volume), regulation is carried out in which the pressure difference between the inspiratory and expiratory pressures is also increased. In total, therefore, a greater increase takes place in the inspiratory pressure (IPAP) than the expiratory pressure (EPAP), although the latter is likewise increased. According to the invention, therefore, it is possible to successfully treat both symptoms simultaneously.

Another application example which may be mentioned is therapy when there is COPD (chronic obstructive pulmonary disease). For therapy adjustment of this chronic obstructive pulmonary disease, the necessary therapy pressures cannot be adjusted manually over several hours by trained specialists. Rather, the process for the therapy adjustment must be simplified. According to the method according to the invention and the corresponding breathing device, instead of continuous monitoring by specialists, only the pressure limits which the patient still tolerates are adjusted. Furthermore, the therapeutic aim is specified, for example avoiding obstruction and achieving a minimum tidal volume (setpoint tidal volume). The pressures necessary for the therapy are preferably determined independently by the device, the regulation being adapted in such a way that the setpoint value of the tidal volume is adjusted and the limit values for the pressures used are complied with. The device may, for example, automatically adapt the respiratory frequency and generate additional mandatory respiratory cycles.

For the two applications mentioned by way of example, the method and the breathing device according to the invention offer further advantages because of the preferred automatic adjustment of the therapy pressures adapted to requirements. If the constraints for the therapy and regulation change, for example because the patient becomes ill, because his weight changes, because of taking medicine or because of alcohol consumption, the therapy pressures can be adapted according to requirements, and an optimal therapy can thus be achieved.

In one preferred embodiment of the method, an expiratory pressure which is less than the inspiratory pressure is generated, so that a pressure difference is formed. Preferably, a lower and an upper pressure limit, within which the pressure can respectively be varied, applies for the inspiratory pressure as well as the expiratory pressure.

In one preferred embodiment of the invention, the pressure difference is regulated until the air volume received by the patient is equal to the setpoint value of the tidal volume. The equalization of the current air volume to the setpoint tidal volume is carried out either over one or more respiratory cycles of the patient or by means of the respiratory minute volume of the patient. Preferably, the mandatory ventilation of the patient is in this case also adapted to existing spontaneous respiration of the patient, so that the inspiratory pressure is generated during the inhalation of the patient and administered by means of a respiratory mask, and during exhalation the expiratory pressure is applied to the respiratory mask.

Preferably, an inhalation and an exhalation are detected by the control unit of the breathing device by cyclic measurement and evaluation of one or more respiratory parameters. The patient's instantaneous tidal volume is measured from the detected inhalation and exhalation and compared with the setpoint value of the tidal volume. In the event of a deviation of the instantaneous tidal volume, or the tidal volume determined over a predetermined time or number of respiratory cycles, comparison is carried out with the corresponding setpoint tidal volume and the pressure is adapted in the event of a deviation. In particular, the inspiratory pressure or the pressure difference between the inspiratory pressure and the expiratory pressure is increased is the set point value is fallen below. The variation of the inspiratory pressure and/or the pressure difference is preferably carried out within the predetermined pressure limits, if there are such.

Preferably, the detection of inhalation and/or exhalation of the patient is carried out automatically with the aid of patient-specific or device-specific parameters, which are preferably adjustable. Patient-related parameters may in this case be for example the typical volume, the typical respiratory flow, the typical frequency, or a typical inspiration duration or expiration duration. The typical values may be taken either by measurement and observation, i.e. from the history, or may be stored as predefined values. The overall leakage of the system, i.e. the intentional leakage at the respiratory mask or an undesired leakage due to poor or incorrect placement of the respiratory mask may be used as device-specific parameters. Automatic triggering, i.e. the sensitivity for the detection of inhalation and exhalation, may also be deduced from the current pressure profile.

Preferably, the expiratory pressure is adapted automatically with the aid of a predetermined therapeutic aim. If the comfort is intended to be increased, for example, a lower expiratory pressure ought to be selected. Adaptation of the exhalation pressure may be carried out both up and down. Aims which are pursued by the adaptation are, for example, treatment of obstructions of the airways, increase of the cardiac output, optimization of the respiratory minute volume or reduction of side-effects, besides the aforementioned increase in comfort.

Preferably, the adjustment is carried out within pressure limits for the expiratory pressure. Besides this, pressure limits may generally be adjusted for the minimum and maximum pressure difference. The pressures for the inspiratory pressure are then obtained computationally and may be determined, represented and/or stored in a breathing device.

The combination of the automatic adaptation of the expiratory pressure with regulation of the tidal volume offers, in particular, advantages for OHS patients (obesity hypoventilation syndrome patients). By the combination, the titration outlay for finding the specific pressures can here be reduced significantly. Furthermore, the invention allows continuous adaptation to the patient's therapy requirement, which may vary either slowly, for example in the course of illness or in the event of a weight change, or rapidly, for example because of a change in the patient's position during the night. Furthermore, both the requirement of the pressure for clearing the upper airways, i.e. adaptation of the expiratory pressure against the obstructions, as well as the requirement for pressure assistance, namely the change in the pressure difference (IPAP minus EPAP) against hypoventilation, normally also change.

In one preferred embodiment, besides the change in the tidal volume, the respiratory frequency for the mandatory ventilation is also regulated. Preferably, in this type of mandatory ventilation, automatic regulation of the respiratory frequency is carried out as a function of the patient's spontaneous frequency, which is determined by the device. Preferably, the spacing of the mandatory respiratory cycles from one another and from the last spontaneous respiratory cycle is determined automatically. For example, the breathing device which uses the method according to the invention may determine the mandatory respiratory frequency as a percentage of the spontaneous respiratory frequency or as a fixed delta from the spontaneous respiratory frequency, i.e. with a fixed difference. As an alternative, iterative acceleration or retardation of the frequency is also possible, with the aim of achieving a higher or lower ratio of spontaneous respiratory cycles. Automatic frequency regulation in combination with the regulation of the tidal volume thus allows overall an improved regulation of the respiratory time volume, or the respiratory minute volume. Furthermore, as an alternative or in addition, minimization of the respiratory stress may also be used as a therapeutic aim.

In a combination of the regulation of the tidal volume with regulation of the anticyclic servoventilation, the setpoint value of the tidal volume may be stored as a lower limit value. Preferably, in the event of a tidal volume above the limit value, i.e. above the setpoint tidal volume, an additional anticyclic pressure reaction is carried out in order to counteract variations of the tidal volume. In this case, for example, either a longer average of the respiratory volume may be formed and then a predetermined percentage (for example 95% or 90%) may be adopted as a target value, or alternatively a variation in the respiration may be counteracted by reacting with stronger pressure assistance in the event of a falling volume; in the case of an increasing tidal volume, the pressure assistance is reduced.

In conventional devices which offer a method of pure servoventilation, a tidal volume or setpoint tidal volume is not specified. Although the devices generally find the target volume automatically, this is however only possible when the patient's average volume is sufficiently large, as in the case of pure periodic respiration. If, however, a respiratory insufficiency also occurs, as is often present as a pulmonary edema in the case of cardiac patients, the average respiration may also be insufficient to achieve good blood gas values. By the combination with a rigidly predetermined setpoint tidal volume, a lower limit is therefore established for the volume automatically found from the servoventilation, below which the pressure assistance, and optionally also the frequency assistance, is increased in any event.

In one preferred embodiment, the applied pressure difference between the inspiratory pressure and the expiratory pressure is varied and adapted as a function of the volume difference between the patient's currently measured tidal volume and the predetermined setpoint tidal volume. Particularly preferably, adaptive adaptation may be carried out.

In the case of known tidal volume regulations, the pressure difference varies. In general, in this case a ramp gradient for the change in the difference per second is specified. In the case of a rigidly adjusted pressure change as a function of time, the target volume (setpoint tidal volume) is achieved earlier for a smaller pressure difference than for a larger pressure difference. In this case, under certain circumstances, reaching of the setpoint value may even be excluded. Such rigid adaptation reduces not only the comfort for the patient but also the breathing efficiency.

According to the invention, the gradient of the pressure increase is particularly preferably adaptively adapted to the pressure difference. This may for example be done using a predetermined regulating time, within which the pressure must be adapted. Such a time span is also referred to as a ramp time. As an alternative, a percentage of the inspiration and expiration may be used. It is advantageous in this case that the pressure difference, the respiratory frequency and the inspiration to expiration ratio of the patient adapt automatically. As another possibility, control may be carried out by means of a predetermined pressure profile. For example, it is possible to specify a pressure profile over a plurality of support points. The profile is preferably configured in such a way that the resulting setpoint pressure profile follows the patient's respiratory flow contour.

In one preferred embodiment, the method according to the invention makes it possible to monitor the reaching of the setpoint value of the tidal volume. Preferably, an alarm signal may be generated and emitted. Such a signal is, for example, an audible signal or an optical signal.

In one preferred embodiment, the determination of the tidal volume is carried out by measuring the patient's inspiratory gas flow, which is determined by determining the total gas flow output by the device and the gas flow output via an existing leak, the so-called leakage gas flow. In one particularly preferred embodiment, the patient's "dead space volume", i.e. the regions not used for the gas exchange, for example trachea and upper airways etc., may also be taken into account in order to determine the tidal volume.

Great requirements are placed on the calculation of the tidal volume, since correct determination of the tidal volume is the most important prerequisite for maximally accurate and error-free regulation of the volume. Preferably, this deviation should be less than 20% or less than 15%. In order to determine the volume, time periods of inspiration and expiration may be determined from the profile of the patient flow. Preferably, either the inspiratory patient flow or the expiratory patient flow is summed over a predetermined time and subsequently averaged correspondingly. It is also possible, however, to measure the flow (gas flow) only over one respiratory cycle. In order to be able to measure the flow very accurately, the device subtracts the desired and undesired leakage from the so-called device flow. The device flow is the total gas flow which is delivered by the device in the breathing tube. The desired leakage may, for example, be determined from the delivered therapy pressures and the mask characteristics, which is often represented as an output flow as a function of the pressure. The undesired leakage, for example incorrect placement of the respiratory mask, may for example be derived by forming the difference of the inspiratory and expiratory raw volumes and the desired leakage. By these measures, the respiratory gas volume provided to the patient can be calculated very accurately.

Since only the alveolar volume, and not the "dead space volume" formed by the trachea and the upper airways and other body parts, contributes to the gas exchange in the lungs, efficient calculation of the relevant volume may, for example, be formed by estimation of the "dead space volume". In this case, the volume per respiratory cycle is always considered. The higher the respiratory frequency is, the greater the fraction of "dead space volume" therefore also is, and the smaller is the effective volume available for the gas exchange for the patient. The dead space volume may, for example, be estimated from the patient's height or determined by means of a $CO_2$ measurement. Preferably, it is possible to input the dead volume directly to the device, so long as it is known or determined as a fixed fraction of the tidal volume for a normal respiratory frequency.

The breathing device according to the invention comprises a respiratory gas source for generating a gas pressure for a patient, which is delivered by means of a respiratory mask. The device comprises a measuring unit for measuring a measurement quantity characteristic of inhalation and exhalation, as well as a control unit which determines the patient's tidal volume from the measurement quantity. In the control unit, the current measurement value of the tidal volume is compared with a setpoint value of the tidal volume (setpoint tidal volume). According to the comparison, regulation of the respiratory gas source is carried out in such a way that the generated gas pressure is made available until the setpoint value of the tidal volume is reached. In addition, further regulation is carried out of a breathing parameter characteristic of the patient's breathing, so that a corresponding regulating signal is likewise delivered to the respiratory gas source. The setpoint value of the tidal volume may be rigidly predetermined, or correspondingly existing parameters or measurement quantities may be currently determined and modified.

For example, the setpoint tidal volume required for a patient, which may be both the volume for a respiratory cycle and a minute volume, may be determined in the device or according to the invention automatically by means of a formula or a table, which may be stored in the device. In particular, the determination of the setpoint tidal volume is carried out by entering height or body weight or a corresponding ideal weight of the patient for the entered height. As an alternative, the tidal volume or minute tidal volume (minute respiratory volume) may be determined automatically in a learning phase from the patient's blood gases, for example by temporarily connecting a measuring device or an estimating device for the oxygen or $CO_2$ content of the blood.

Preferably, the breathing device has an alarm unit in order to emit an alarm signal. If the tidal volume departs from the minute-reserved tidal volume (respiratory minute volume) or the respiratory frequency departs from at least one of the threshold values, e.g. adjustable in the device, for a predetermined time, then an alarm is triggered. In particular, an alarm takes place when the setpoint tidal volume cannot be reached, e.g. after a predefined period of time, even though an increase in the pressure assistance has been carried out by an increased inspiratory pressure or an increased pressure difference or by an increase in the respiratory frequency. The patient or the user of the device, for example medical personnel, is therefore made aware of a change in the patient's disease profile or an insufficient selection of the device settings. Preferably, to this end the alarm unit comprises an alarm output unit. Particularly preferably, a loudspeaker or a buzzer is provided. As an alternative or in addition, an optical alarm may be emitted.

Parameters of the patient's current respiration and device settings are output on a visualization apparatus of the device. The visualization unit preferably comprises a display in order to display the parameters or breathing parameters or measurement values or values further processed from measurement values. In particular, these include the tidal volume (volume per respiratory cycle or the tidal minute volume), the respiratory frequency, the inspiratory and expiratory pressures as well as the limit values for these pressures, the target volume or setpoint tidal volume, the type of pressure assistance, for example the pressure difference, or a background frequency which may exist, in order to adapt mandatory ventilation to this frequency. With the aid of these parameters and characteristics, the user, patient or doctor can optimize the device settings. Preferably, the breathing device comprises an interface in order to transmit the values to be displayed to an external visualization device. External storage of the data is therefore also possible.

For storage, a memory unit is preferably provided, in order to store the measured values, the characteristic breathing parameters, the alarms, the respiratory volume or the adjustment parameters. An optional computation unit is used for statistical evaluation of the parameters. Of course, other adjustment parameters or respiratory characteristics may also be recorded, stored or represented. Optionally, they may be transmitted to a server computer, for example via a cabled or wireless interface. Statistical characteristics may then be determined from these data by means of the computation unit, in order for example to verify and check the effectiveness of the regulations. Of course, the outcome of a longer therapy may also be evaluated and assessed. Besides the parameters mentioned above, quantities like the number of respiratory cycles, duration of the therapy phases, percentage duration of the phases with the target volume or setpoint tidal volume being exceeded or fallen below, are also of interest and may be processed, stored or represented.

The cabled or wireless interface is provided inside the device or in the region of the device housing. As an alternative, an interface module which provides further interfaces may be attached, for example by latching, by means of a first interface. By means of the interface, a connection to a server or a network may be established, via which data can be read out from the device, the device can be configured or a service function can be carried out. Technologies can be GSM, GPRS, UMTS, LTE, Sigfox, LOLA, Bluetooth or similar wireless standards.

In a preferred embodiment, the breathing device has an operating unit, which comprises one or more man/machine interfaces and preferably has a touchscreen display. By means of such a display, simple user-friendly operation of the device is possible. Furthermore, in addition or as an alternative, buttons, a rotary knob or similar switches or sliders may also be provided. The selection of parameters to be adjusted may, for example, be carried out by means of selection lists or selection tables or so-called menus, which may be displayed on the display. Particularly in the case of touchscreen displays, a selection may be carried out very simply for the patient. The displaying of the individual parameters or the selection of individual parameters may be represented in different display planes or different display fields.

For example, the parameters for ventilation with a tidal volume and a setpoint value of the tidal volume may be represented in a different menu plane or a different display region than pure device parameters or service parameters, which may for example also be secured by a password.

In another preferred embodiment the breathing device comprises a display, which is angled relative to the base of the device. Preferably, the inclination of the display is not at a right angle or parallel to the base; the inclination angle is thus neither 90 degrees nor zero degrees. Particularly preferably, the display is tilted relative to the base with an oblique angle of between 20 degrees and 70 degrees. Owing to the oblique positioning of the display, particularly in the preferred angle range, reading of the parameters can be carried out conveniently when lying, standing or sitting. A display which is variable in its inclination, and in general can be tilted between zero degrees and 90 degrees, is particularly preferred. Besides horizontal tilting, vertical tilting may also be advantageous.

In one particularly preferred embodiment, the brightness of the display can be adjusted. In particular, automatic dimming of the display brightness may be carried out, for example after a certain time after the last input or in a predetermined range of between one minute and several minutes. The brightness of the display may be adapted automatically to the ambient brightness, so that the patient can sleep undisturbed.

By means of an interface (wireless or jack), a pulse oximeter may be adapted for therapy monitoring or for learning the correct setpoint tidal volume or setpoint minute volume, or setpoint alveolar respiratory volume. As an alternative or in addition, CO2 meters, for example a ptCO2 meter and/or an enhanced diagnostic device may be connected. The enhanced diagnostic device registers effort, body position, pulse frequency, PTT, pulse wave amplitude, autonomous arousals, sleep stages or an indicator of heart disease.

The breathing device according to the invention comprises a respiratory gas source for generating a gas pressure for a patient, which is delivered by means of a respiratory mask, a measuring unit for measuring a measurement quantity characteristic of inhalation or exhalation, and a control unit which determines the patient's tidal volume from the measurement quantity, compares this with a setpoint value of the tidal volume and regulates the respiratory gas source in such a way that the generated gas pressure is made available until the setpoint value of the tidal volume is reached, in addition, further regulation of a breathing parameter characteristic of the patient's breathing being carried out and a corresponding regulating signal being delivered to the respiratory gas source. According to the invention, the regulation of one or more breathing parameters characteristic of the patient's breathing is carried out. The breathing parameters may be individual parameters such as pressure, flow or volume, frequency, or alternatively complex patterns.

According to the invention, regulation is carried out of the tidal volume and/or the frequency and/or the EPAP and/or the IPAP and/or the PEEP and/or ramps of the EPAP and/or ramps of the IPAP and/or the inspiration time and/or the expiration time and/or the expiration volume and/or the cough assistance and/or the anticyclic servoventilation regulation. For example, EPAP and/or PEEP are selected in such a way that obstructions of the upper airways are avoided and the setpoint value for the tidal volume is furthermore reached.

For example, EPAP and/or PEEP are selected in such a way that obstructions of the upper airways are avoided and the setpoint value for the tidal volume is furthermore reached, the frequency likewise being adapted. When the tidal volume and therefore the patient's minute volume decrease, the respiratory frequency is increased. When the EPAP rises, the respiratory frequency is likewise increased in order to reach the tidal volume.

For example, a control characteristic with a minimum expiration time or a minimum expiration volume is furthermore specified. To this end, the flow or the pressure or the volume of respiratory gas is recorded as a measurement quantity. A pressure increase to the IPAP pressure is suppressed until the minimum expiration volume or the minimum expiration time is reached.

The control increases the respiratory gas pressure in the inspiration, for example, when a signal representing the respiratory flow or the respiratory cycle volume indicates that the patient's expiration process is not ended.

The control increases the respiratory gas pressure in the expiration, for example, when a signal representing the respiratory flow or the respiratory cycle volume indicates that the patient's expiration process is not ended.

As an alternative, the control is provided with trigger signal suppression, which disables a pressure increase for a predeterminable blocking time, which begins with an expiratory pressure reduction.

As an alternative, the minimum expiration time or the minimum expiration volume is selected as a trigger blocking time. The minimum expiration time may also last until a signal representing the respiratory flow or the respiratory cycle volume indicates that the patient's expiration process is ended.

The breathing device according to the invention comprises a respiratory gas source for generating a gas pressure for a patient, which is delivered by means of a respiratory mask, a measuring unit for measuring a measurement quantity characteristic of inhalation or exhalation, and a control unit which determines the patient's tidal volume from the measurement quantity, compares this with a setpoint value of the tidal volume and regulates the respiratory gas source in such a way that the generated gas pressure is made available until the setpoint value of the tidal volume is reached, in addition, further regulation of at least one breathing parameter characteristic of the patient's breathing being carried out and a corresponding regulating signal being delivered to the respiratory gas source. To this end, the breathing device has a control unit which causes the respiratory gas source to provide at least one elevated pressure level starting from a base pressure level, the breathing device furthermore having a counter which is activated with the transition to the maximum pressure level in order to count a predeterminable period of time, after which the respiratory gas source is caused by the controller to reduce the respiratory gas pressure, and the control unit furthermore being configured in order to cause an output device to output a perceptible signal.

The apparatus according to the invention therefore assists patients during coughing in that, starting from the inhalation pressure (IPAP), an increased respiratory gas pressure is provided so that inhalation deeper than normal breathing is induced and the lungs and thorax are pre-tensioned. In order to carry out coughing, good coordination by the patient with a pressure maneuver at the device is necessary. To this end, the patient must close his glottis at the correct moment before the pressure falls again, in order to keep the air in the lungs for a moment.

By a signal generated by the apparatus, which sounds when reaching a pressure plateau with an elevated respiratory gas pressure, the patient can determine the best time to close his glottis and synchronize himself optimally with the device, and subsequently himself actively carry out coughing. In terms of device technology, optimal coughing is assisted by rapid reduction of the pressure following the insufflation.

The apparatus according to the invention is advantageously distinguished in that the predeterminable time period is in the range of from 0.250 to 6 seconds. This period of time offers the patient sufficient time to prepare for coughing by closing the glottis.

For the method according to the invention for controlling a respiratory gas source with a control unit for a patient's breathing, comprising regulation of the patient's tidal volume by providing and applying inspiratory pressure and simultaneous regulation of a further breathing parameter, all alternatives mentioned above for the enhanced regulation of one (or more) further breathing parameters likewise apply accordingly. In this case, simultaneous regulation means regulating at least two breathing parameters in a unit of time or regulating at least two breathing parameters while taking into account the respective cross-influences or dependencies.

According to the invention, a pause mode is also optionally provided. Here, a pause need not mean that the mask is removed during it. It is also possible for the patient to continue the therapy but to use the pause in order to relieve himself of high therapy pressures or slowly to become re-accustomed to spontaneous respiration. Preferably, the patient initiates the pause mode himself. After activation of the pause mode by the patient, the breathing device reduces the ventilation stepwise or continuously. In this case, an intermediate re-increase of the ventilation is also possible, although following this the ventilation is returned to the pause mode. This is done by reducing the IPAP and/or EPAP and/or the frequency and/or the volume.

The slow reduction may be carried out linearly: this means a fixed reduction of at least one pressure in hPa per respiratory cycle or per unit time, preferably between 0.1 and 10 hPa per minute.

The slow reduction may be carried out nonlinearly: this means, for example, a reduction of at least one pressure in % per respiratory cycle or per unit time, preferably between 0.5 and 50% per minute.

The slow reduction may be carried out on a success basis: after one reduction in % or hPa, a success event must occur in order to carry out the next reduction step. Success events may be: pressing a button/voice input/other trigger event by the user, reaching or maintaining a target value after a target time, for example no reduction in respiratory volume or SpO2 or respiratory frequency after a measurement time of between 10 s and five minutes, or no CO2 increase in this time.

For all embodiments of the invention, it furthermore applies that, in the regulation of at least two breathing parameters, prioritization may be carried out by the user or automatically, in order to weight one breathing parameter more strongly.

BRIEF DESCRIPTION OF THE DRAWINGS

The invention will be explained below with the aid of drawings, in which.

In the description of the figures (unlike in the text above), tidal volume always refers to the respiratory volume per respiratory cycle, while the respiratory minute volume or minute volume describes the tidal volume per minute.

DETAILED DESCRIPTION OF EMBODIMENTS OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
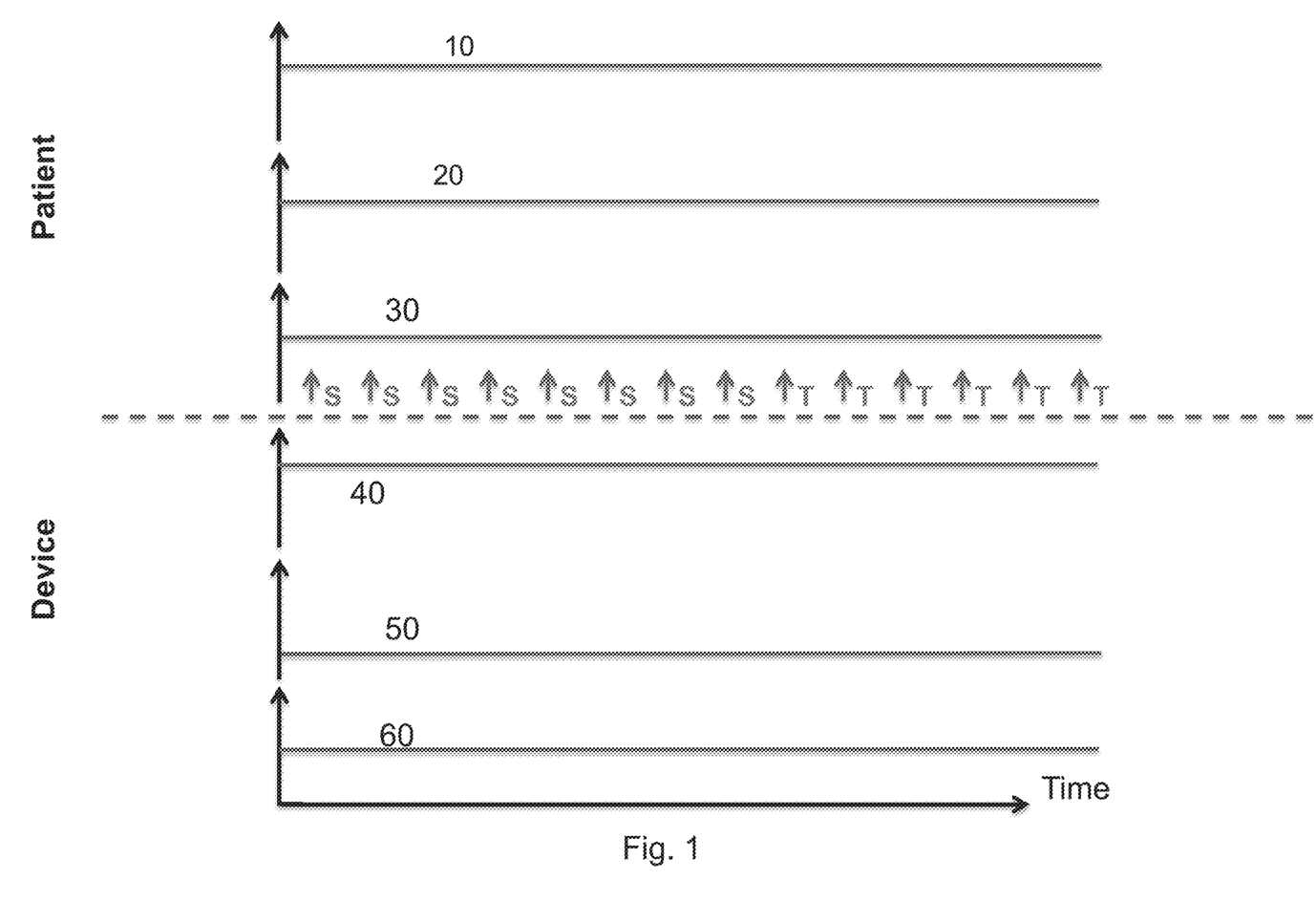
FIG. 1 shows the time profile of the tidal volume, minute volume and the frequency for a patient in a stable situation, when breathing takes place with a predetermined pressure difference, as well as the time profile of the inspiratory pressure, the expiratory pressure and the pressure difference.

FIG. 1 shows in the upper region three time profiles in the case of stable titration of the patient by means of a breathing device 70. The tidal volume 10 per respiratory cycle, the respiratory minute volume 20 and the respiratory frequency 30 of the patient are shown. In addition, it is represented at the lower edge of the upper part whether spontaneous respiration is being carried out by the patient (↑S) or time-controlled ventilation (↑T), which is initiated by the breathing device 70. In this case, a background frequency is correspondingly specified by the device 70 and complied with during the regulation.

In the lower part of FIG. 1, the time profile of the inspiratory pressure 40 (IPAP), of the expiratory pressure 50 (EPAP) and the pressure difference 60 are represented. Since all the characteristics are represented as horizontal straight lines, constant additional ventilation of the patient is being carried out, which leads to a constant respiratory volume 10 and respiratory minute volume 20.

Figure 2:
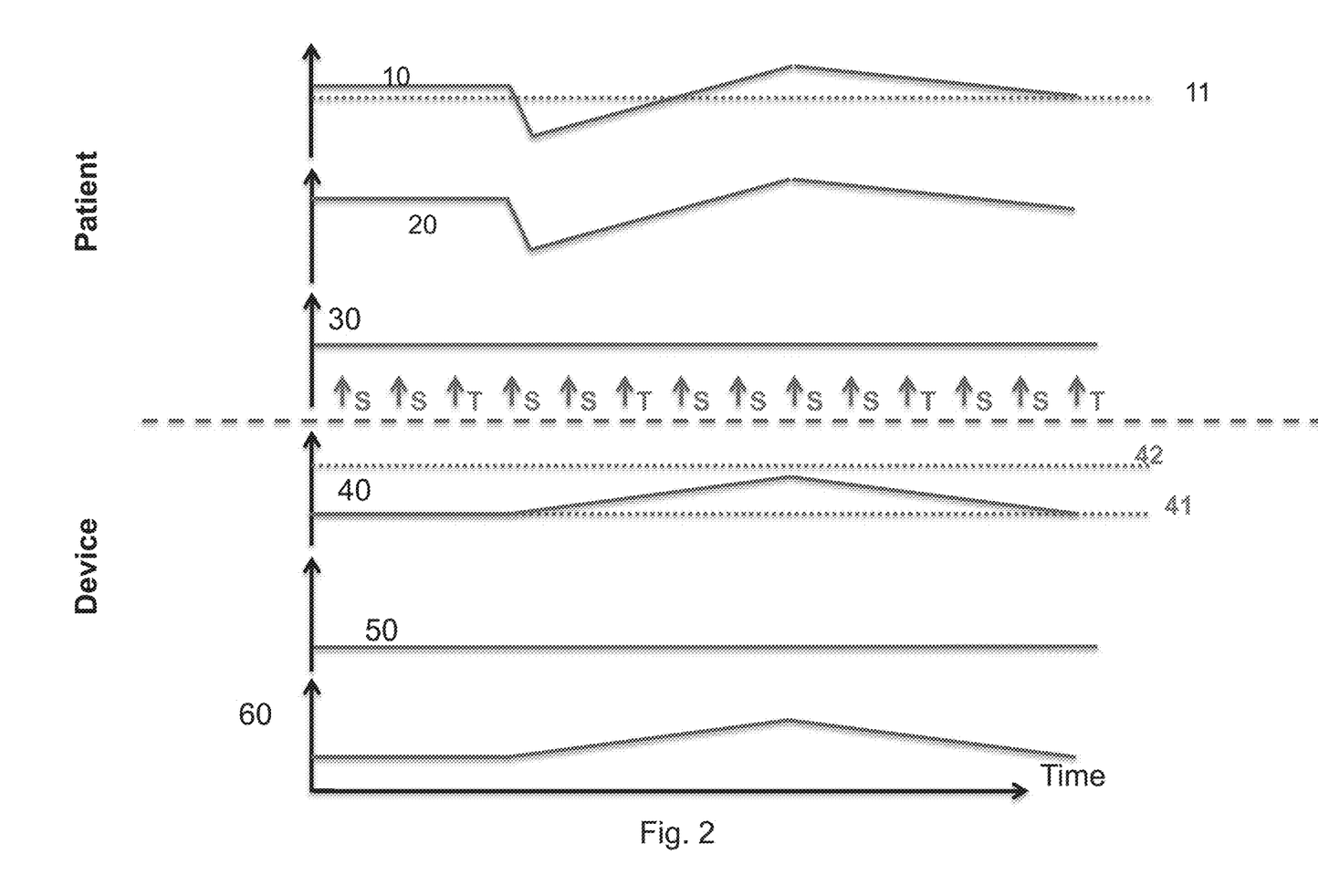
FIG. 2 shows the time profiles of FIG. 1 with activated tidal volume regulation.

FIG. 2, on the other hand, shows the time profile in the case of activated tidal volume regulation. If the tidal volume 10 and the minute volume 20 of the patient decrease, then the decrease is registered by the breathing device 70 and the inspiratory pressure 40 is increased. The expiratory pressure 50 for opening the airways remains constant. This leads to an increase in the pressure difference 60. As soon as the inspiratory pressure 40 increases, the tidal volume 10 of the patient also increases. When it exceeds the setpoint value 11 of the tidal volume, the regulation begins again, for example after a certain dead time. The inspiratory pressure 40 is reduced until it decreases back to its initial value (lower limit 41). The inspiratory pressure 40 is in this case regulated within the predetermined pressure limits (IPAPmax as an upper limit 42 and IPAPmin as a lower limit 41). In FIG. 2, it can be seen that in the regulation shown here the maximum upper limit 42 of the inspiratory pressure 40 has not yet been reached. EPAP 50 and/or PEEP are furthermore or in addition regulated in such a way that obstructions are substantially avoided. The tidal volume regulation is in addition improved by entering the patient's height, in order to calculate the anatomical dead spaces therefrom and take them into account in the ventilation. In addition, further patient data such as age or weight or sex may be entered. Taking the patient data into account, a target value for the alveolar ventilation is calculated and the EPAP 50 and/or IPAP pressure 40 is controlled in such a way that the target value is ideally reached.

Figure 3:
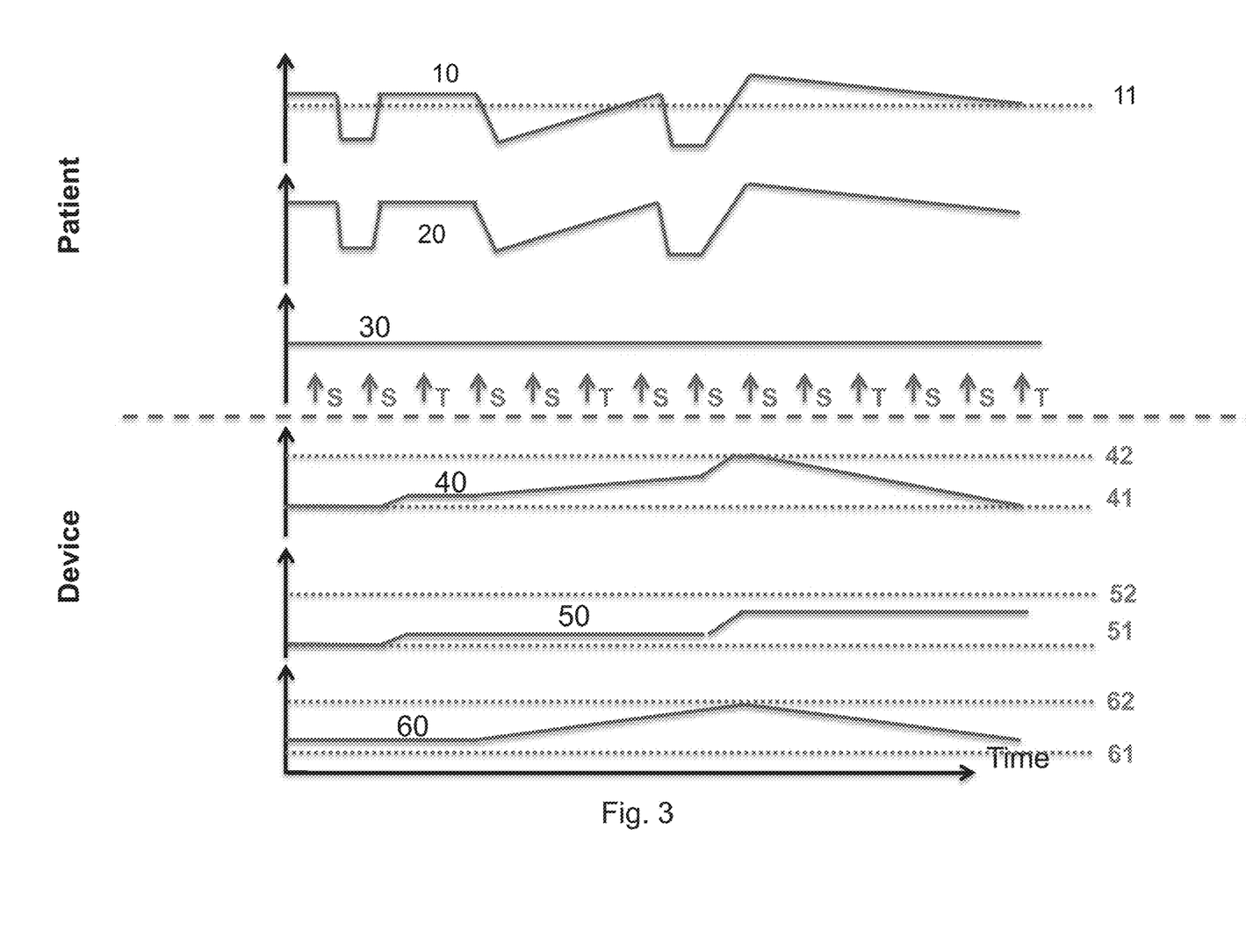
FIG. 3 shows the time profiles with activated tidal volume regulation in combination with auto-EPAP regulation.

FIG. 3 shows the combination of tidal volume regulation and auto-EPAP regulation. In the upper diagram of FIG. 3, it can be seen that the tidal volume 10 and the minute volume 20 of the patient initially decrease abruptly. This may, for example, take place because of additional obstructions of the upper airways, for example in the case of apnea. After a certain period of time, the tidal volume 10 increases again automatically and returns to the previous value, which in this case lies above a setpoint tidal volume 11 (dashed line).

Here as well, the regulation reacts with a time delay. The inspiratory pressure 40 is increased in order again to prevent such apnea. At the same time, to the same extent, the expiratory pressure 50 is increased. This pressure 50 may also take place within predetermined minimum and maximum values, i.e. between a set lower limit 51 and a set upper limit 52. Since both the inspiratory pressure 40 and the expiratory pressure 50 has been increased (to the same extent), the pressure difference 60 initially remains constant.

In the further course of time, a second apnea takes place, in which the tidal volume 10 and the minute volume 20 of the patient decrease. A further increase of the inspiratory pressure 40 is then carried out, the expiratory pressure 50 remaining constant. Consequently, the pressure difference 60 also increases. Because of this regulation and the administration of time-controlled ventilation, the tidal volume 10 and the minute volume 20 increase again. It again reaches the setpoint value 11 of the tidal volume. Subsequently, a further reduction of the tidal volume 10 occurs, for example due to another apnea. The inspiratory pressure 40 is thereupon increased until the maximum limit value 42 is reached. Furthermore, the expiratory pressure 50 is increased in order to counteract the obstructions. By these measures, the tidal volume 10 consequently increases again up to above the desired setpoint tidal volume value 11. The inspiratory pressure 40 is thereupon reduced, the expiratory pressure 50 remaining at a higher level but still within the pressure limits. In this way, rapid adjustment of the tidal volume 10 of the patient can be made possible.

In FIGS. 1 to 3, it can be seen that the frequency regulation, and therefore the frequency with which the breathing device 70 carries out mandatory ventilation of the patient, is independent of the pressure regulation. The control of the pressure is therefore carried out independently of the adjusted frequency regulation; this may be a rigidly predetermined frequency or an adjusted background frequency, which at fixed times carries out ventilation of the patient. According to the invention, provision is also made that the frequency of the patient respiration is determined by sensing 86 and is at least partially used for the calculation of the predetermined frequency. Other measurement quantities which are included in the calculation of the predetermined frequency may be the respiratory minute volume and/or the target volume.

The predetermined frequency is calculated and adjusted in such a way that it adaptively remains behind the frequency of a spontaneously respiring patient, so long as the spontaneous patient respiration lies within a predeterminable or predetermined limit value from the desired setpoint tidal volume value 11. As soon as the spontaneous patient respiration lies outside a predeterminable or predetermined limit value from the desired setpoint tidal volume value 11, the predetermined frequency is calculated and adjusted in such a way that the desired setpoint tidal volume value 11 is reached or the spontaneous patient respiration at least lies again within a predeterminable or predetermined limit value from the desired setpoint tidal volume value 11.

Figure 4:
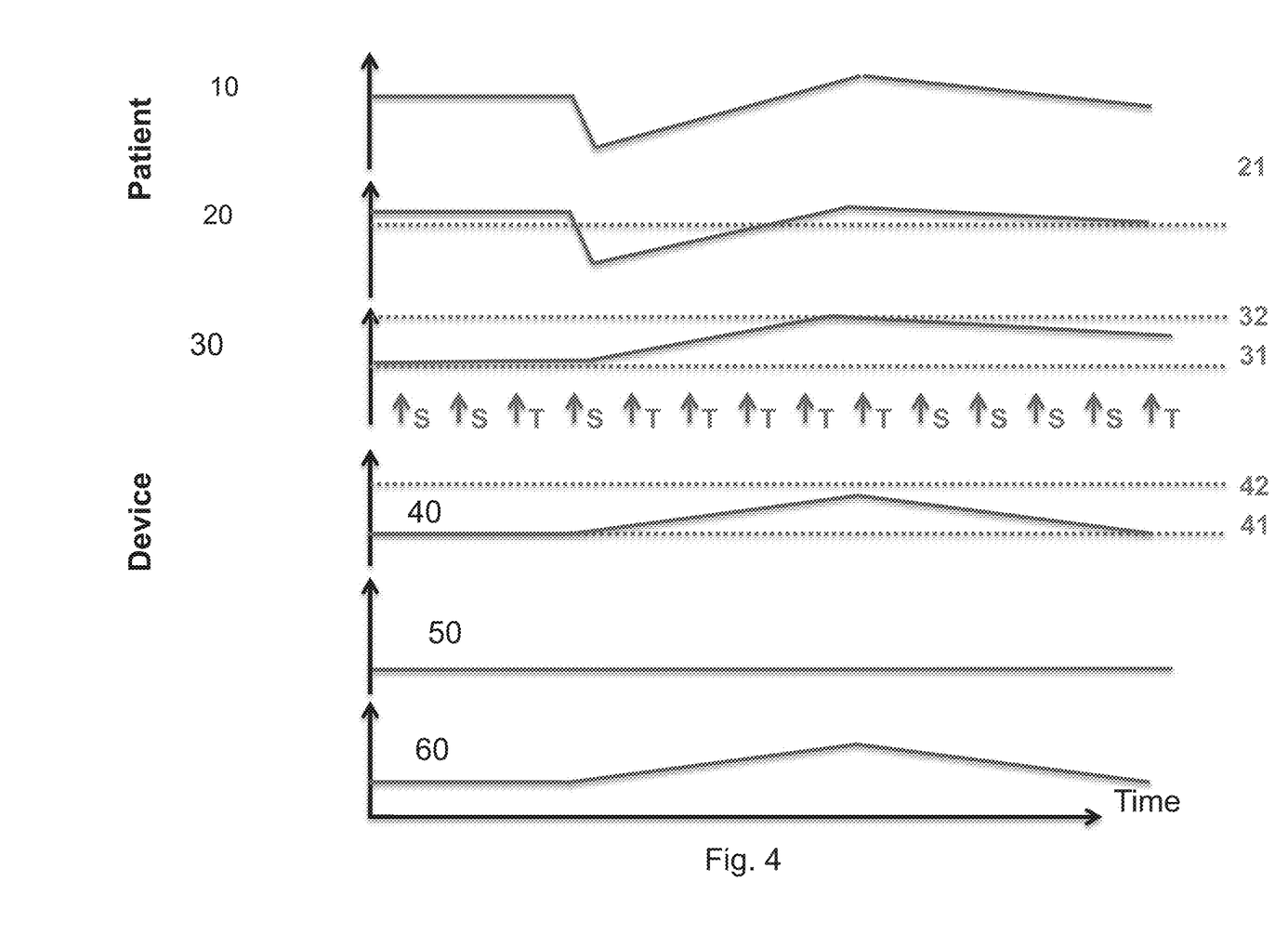
FIG. 4 shows the time profiles of the aforementioned parameters with activated tidal volume regulation and automatic frequency regulation in order to control the minute volume flow.

FIG. 4 shows the combination of the tidal volume regulation with automatic frequency regulation, in order to correct the minute volume 20 of the patient. If a decrease of the tidal volume 10 and therefore of the minute volume 20 of the patient takes place, the respiratory frequency 30 is increased. Preferably regulation of the frequency with which breathing takes place is carried out within an upper limit value 32 and a lower limit value 31. At the same time as the adaptation and increase of the respiratory frequency 30, the inspiratory pressure 40 is also increased. Since the expiratory pressure 50 remains constant, the pressure difference 60 varies in parallel with the inspiratory pressure 40. It should be noted that the device partially compensates for the reduction of the respiratory volume 10 by a higher frequency 30 of the mandatory ventilation. This, however, is paired with an increase of the inspiratory pressure volume 40. As soon as the desired minute volume 20 is reached, i.e. lies above a target minute volume 21, the frequency 30 is reduced again (after a certain regulating dead time). In this case, a slow reduction of the frequency 30 takes place. In addition, with a further delay, a reduction of the inspiratory pressure 40 also takes place until it reaches the predetermined lower limit 41.

Figure 5A:
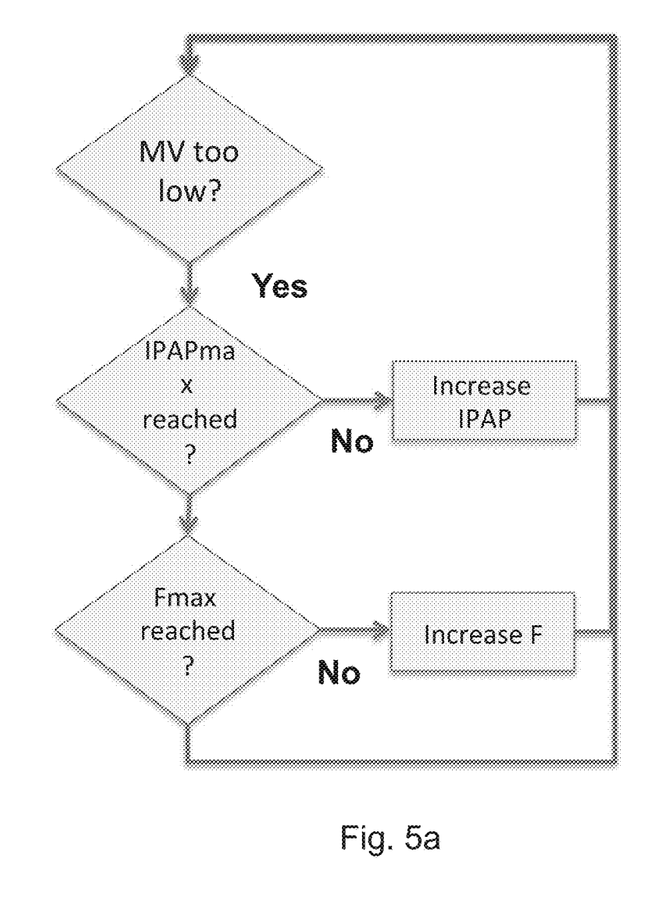
FIGS. 5a-c show flow charts for the combination of tidal volume regulation and automatic frequency regulation in order to control the minute volume in three embodiments.
Figure 5B:
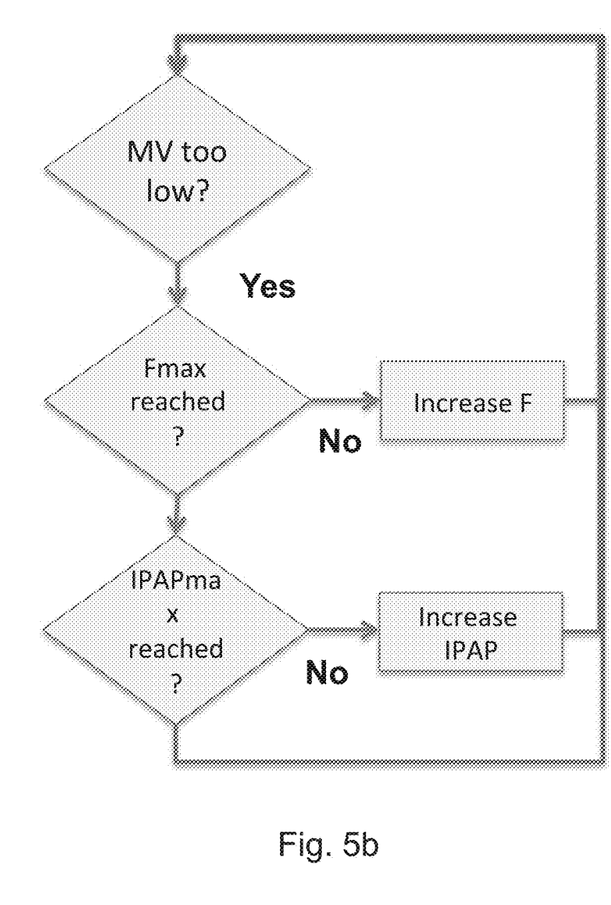
Figure 5C:
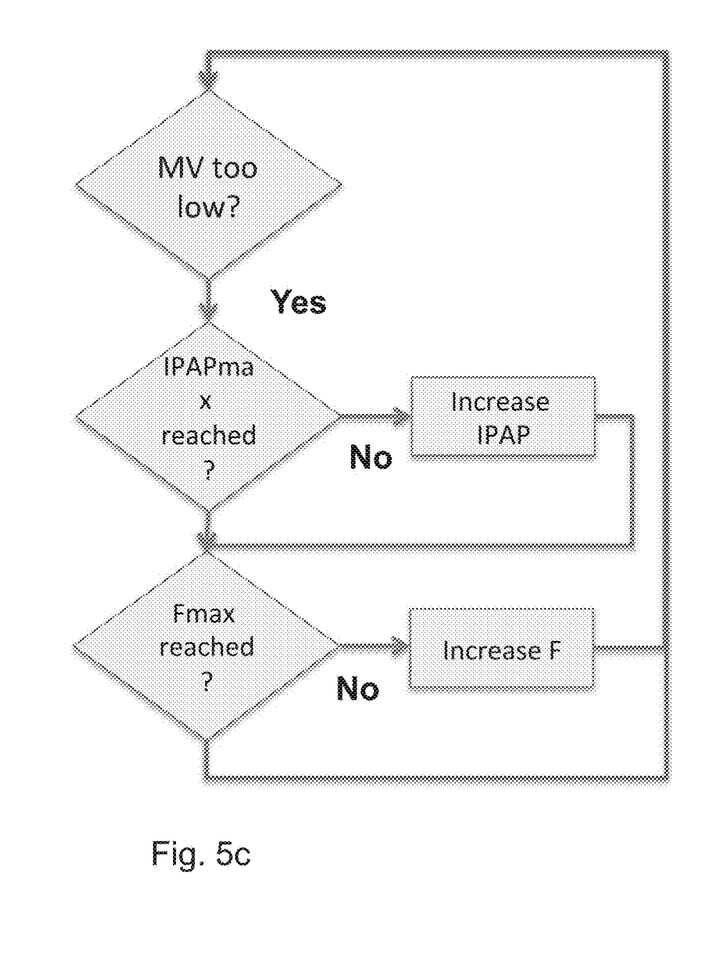

FIGS. 5a-c each show a flowchart of the automatic frequency control paired with tidal volume regulation. FIG. 5a shows the procedure when the regulating focuses on an increase of the inspiratory pressure, and FIG. 5b shows regulation with the focus on frequency regulation. As soon as the minute volume of the respiratory volume is too low, a check is initially made whether the upper limit of the inspiratory pressure (FIG. 5a) or the frequency (FIG. 5b) is reached. If this is not the case, an increase of the pressure or the frequency is carried out. A check is subsequently again made whether the minute volume is too low.

If the allowed limit value has already been reached, a check is made whether the maximum of the corresponding other regulating quantity (frequency according to FIG. 5a or pressure according to FIG. 5b) has already been reached. If this is not the case, an increase of the frequency or the pressure is carried out; otherwise not, since the limit value must not be exceeded. Regulation to generate setpoint tidal volume is then not possible.

FIG. 5c shows a combination of the two regulations. Here again, a check is again made whether the minute volume is too low, i.e. lies below the predetermined limit value. If this is the case, the query is made whether the administered inspiratory pressure has already reached the upper limit and, independently of the result of this query, whether the maximum frequency is already applied. If an upper limit has not yet been reached, an increase of the respective regulating quantity is carried out, so that both the pressure and the respiratory frequency are regulated. In this way, the regulation can be accelerated which ultimately leads to an increase in the patient's comfort.

Figure 6:
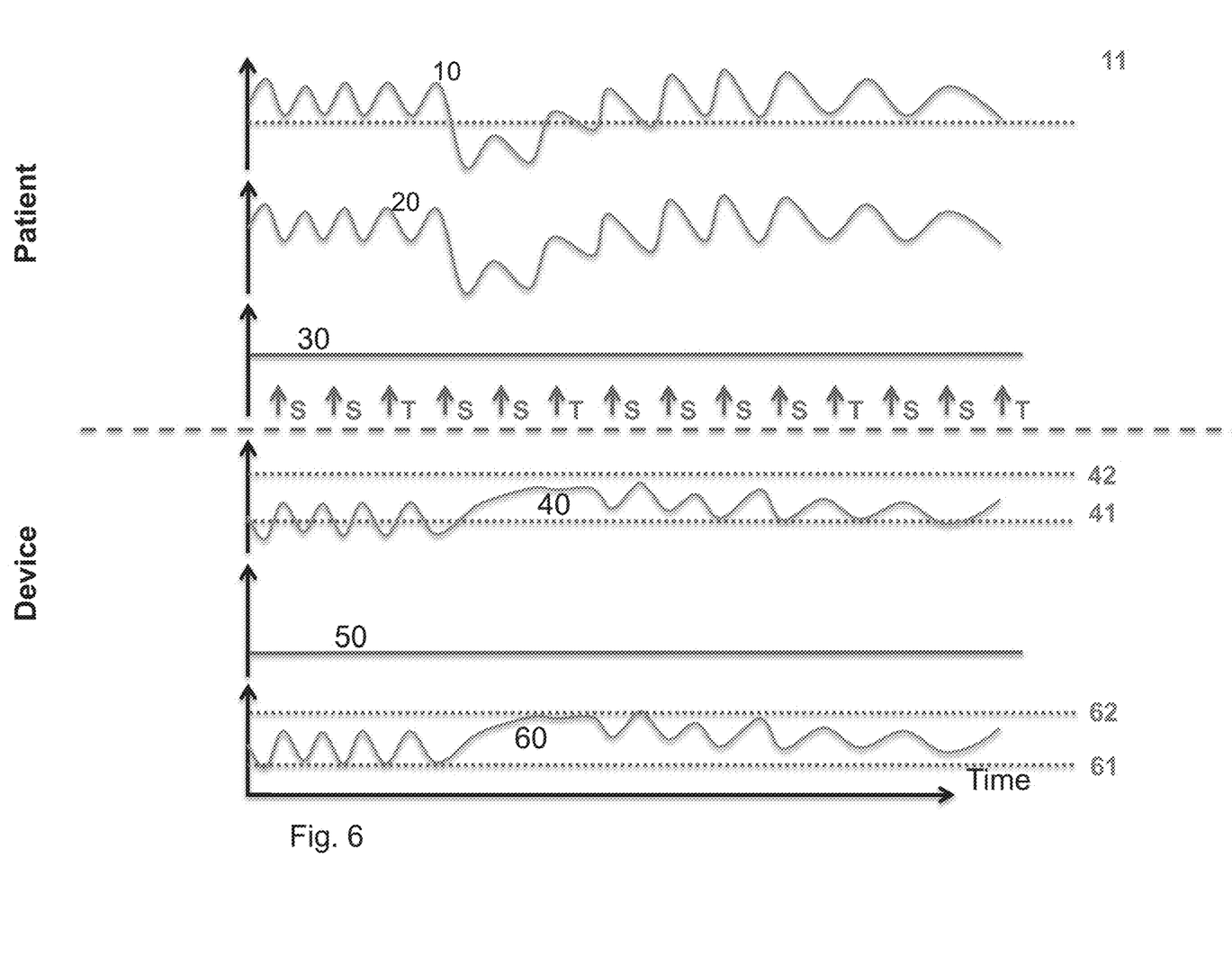
FIG. 6 shows the time profiles with activated tidal volume regulation in addition to anticyclic servoventilation regulation.

FIG. 6 shows the time profile of a combination of the tidal volume regulation and anticyclic servoventilation regulation. The time profiles of the tidal volume 10 and minute volume 20 show typical periodic respiration of the patient with a so-called Cheyne-Stokes syndrome, in which the respiratory volume 10 varies around a particular volume value. In order to compensate for these variations the inspiratory pressure 40 is anticyclically adapted. In the event of an increase in the tidal volume 10, the inspiratory pressure 40 is reduced; in the event of a decrease in the tidal volume 10, the inspiratory pressure 40 is increased. The expiratory pressure 50 remains constant, so that the pressure difference 60 varies in parallel with the inspiratory pressure 40. The inspiratory pressure 40 and the pressure difference 60 are regulated within the predetermined limits (41, 42 and respectively 61, 62).

As long as the patient's periodic respiration lies above a predetermined setpoint tidal volume 11, the regulation of the inspiratory pressure 40 is also carried out around the lower limit value 41. It may even be fallen below in this case, since the lower limit value 41 is established in order to comply with the setpoint tidal volume 11. If the setpoint tidal volume 11 is fallen below, the inspiratory pressure 40 is increased. The anticyclic pressure regulation is stopped and a strong rise of the inspiratory pressure 40 is applied. In this way, the reduction of the air volume 10 (tidal volume) is compensated for. As soon as the patient's tidal volume 10 exceeds the setpoint tidal volume value 11 again continuously, the pressure regulation returns to anticyclic regulation. However, the pressure level is provided with an offset which decreases slowly, so that the inspiratory pressure 40 oscillates around the lower limit value 41. The anticyclic pressure regulation is carried out above the lower limit 41 (IPAPmin).

In this way, it is possible not only to compensate the periodic volume variation of the patient, but also to react rapidly to a reduction of the respiratory volume.

Figure 7:
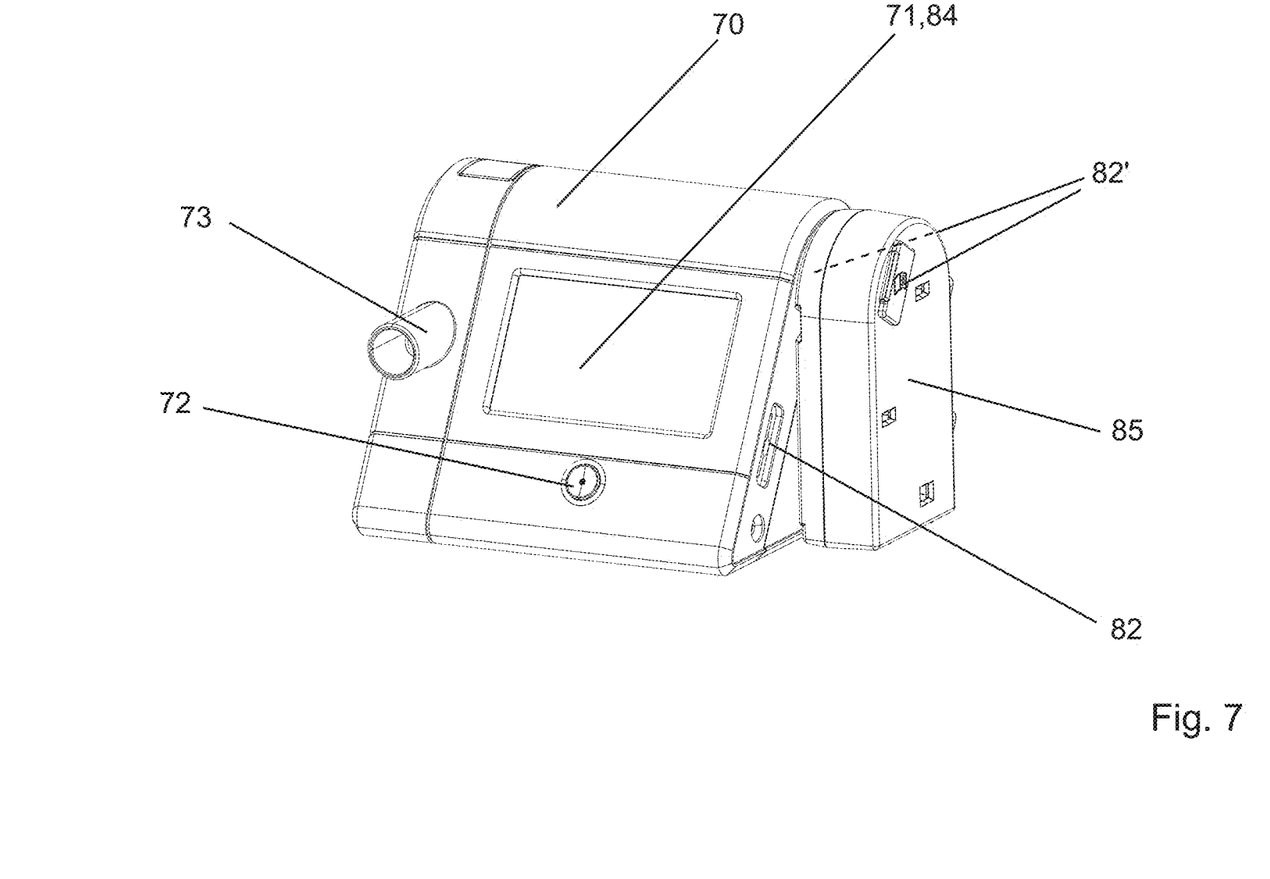
FIG. 7 shows a view of a breathing device having a visualization unit and interfaces.

According to the invention, determination of leaks is also provided. Leaks are to be taken into account since the therapy pressures are fully effective, and the target volumes can be reached, only with a sealed mask 75. If an increase in the leakage is detected by sensors 86, output takes place in the form of a message about the mask sealing defect on the patient during the therapy. This output preferably takes place on the display 71 of the device 70.

FIG. 7 shows the basic structure of a breathing device 70, which is provided with a visualization device 71, at least one operating element 72 and a tube connection 73. A respiratory mask 75 is connected to the tube connection 73, typically by means of a connecting tube 74. The respiratory mask 75 and the connecting tube 74 for the respiratory gas supply of a patient are not represented. The breathing device 70 has an internal respiratory gas source 76 in the form of a fan, as well as a controller 77 of this respiratory gas source 76. In addition, the breathing device 70 also has a measuring unit 78 as well as a memory unit 80. Besides displaying, the visualization device 71 is also used as an operating unit 84 of a man/machine interface in the form of a touchscreen display. The breathing device 70 is typically provided with at least one communication interface 82. The interface 82 is in this case arranged in a side region. The interface 82 is inclined with respect to the horizontal and lies in spatial proximity to the visualization device 71. The breathing device 70 preferably also has a further interface 82', which is used for the coupling of modules 85.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

LIST OF REFERENCE NUMERALS

Item No.
10 tidal volume per respiratory cycle
11 setpoint value of the tidal volume
20 respiratory minute volume
30 respiratory frequency
↑S spontaneous respiration
↑T controlled breathing
40 inspiratory pressure, IPAP
41 IPAPmin, lower limit or starting value
42 IPAPmax, upper limit of IPAP
50 expiratory pressure, EPAP
51 EPAPmin, lower limit of EPAP
52 EPAPmax, upper limit of EPAP
60 pressure difference
61 lower limit of pressure difference
62 upper limit of pressure difference
70 breathing device
71 visualization device, for example display
72 operating element
73 tube connection
74 connecting tube
75 respiratory mask
76 respiratory gas source
77 control unit
78 measuring unit
79 alarm unit, for example loudspeaker, buzzer
80 memory unit
81 computation unit
82 interface
82' interface
83 external visualization apparatus
84 operating units
85 module
86 sensor

What is claimed is:

1. A method for controlling a respiratory gas source comprising a control unit for a patient's breathing, wherein the method comprises regulating the patient's tidal volume by providing and applying inspiratory pressure and simultaneously regulating a further breathing parameter which comprises at least one of
   automatic regulation of respiratory frequency,
   anticyclic pressure reaction regulation,
   regulation of transition pressure between inspiratory pressure and expiratory pressure.

2. The method of claim 1, wherein regulating the tidal volume comprises:

measuring a gas flow or a volume flow,
determining an air volume received by the patient,
establishing a setpoint value of the patient's tidal volume,
generating an inspiratory pressure,
regulating the inspiratory pressure in such a way that the setpoint value of the tidal volume is reached.

3. The method of claim 1, wherein regulating a further breathing parameter further comprises at least one of the following:
regulation of an automatic trigger for detecting exhalation and/or inhalation,
automatic adaptation of exhalation pressure.

4. The method of claim 1, wherein an expiratory pressure which is less than an inspiratory pressure is generated, so that a pressure difference is formed.

5. The method of claim 4, wherein the inspiratory pressure is variable between a lower inspiratory pressure limit and an upper inspiratory pressure limit, and the expiratory pressure is variable between a lower expiratory pressure limit and an upper expiratory pressure limit.

6. The method of claim 4, wherein the pressure difference is regulated until the tidal volume received by the patient is equal to a setpoint value of the tidal volume.

7. The method of claim 1, wherein the regulation of the tidal volume is carried out over one or more respiratory cycles of the patient.

8. The method of claim 7, wherein a mandatory ventilation is adapted to an existing spontaneous respiration of the patient.

9. The method of claim 1, wherein an inhalation and an exhalation are detected by the control unit by cyclic measurement and evaluation of a respiratory parameter, and the instantaneous tidal volume is measured and compared with a setpoint value of the tidal volume, and wherein further an inspiratory pressure or a pressure difference between the inspiratory pressure and an expiratory pressure is increased if the setpoint value is fallen below.

10. The method of claim 1, wherein an expiratory pressure is adapted automatically with the aid of a predetermined therapeutic aim.

11. The method of claim 1, wherein, in the event of additional regulation of a respiratory frequency and mandatory ventilation, automatic regulation of the respiratory frequency is carried out as a function of a patient's spontaneous frequency.

12. The method of claim 11, wherein automatic regulation of the respiratory frequency is variable as a fixed percentage of the spontaneous respiratory frequency, as a fixed difference from the spontaneous respiratory frequency or iteratively in order to generate accelerated or retarded spontaneous respiration.

13. The method of claim 1, wherein a setpoint value of the tidal volume is stored as a lower limit value and, in the event of a tidal volume above the limit value, an additional anticyclic pressure reaction is carried out in order to counteract a variation of the tidal volume.

14. The method of claim 1, wherein an applied pressure difference between an inspiratory pressure and an expiratory pressure is varied as a function of a volume difference between a currently measured tidal volume and a setpoint value of the tidal volume.

15. The method of claim 14, wherein adaptation is carried out with a predetermined ramp time after which the setpoint value is reached and the pressure difference has reached its maximum.

16. The method of claim 14, wherein adaptation is carried out with a predetermined fraction of inspiration and/or expiration or by regulation with a predetermined pressure profile.

17. The method of claim 1, wherein the patient's dead space volume is taken into account in determining the tidal volume.

18. The method of claim 1, wherein simultaneously regulating a further breathing parameter comprises at least automatic regulation of respiratory frequency.

19. The method of claim 1, wherein simultaneously regulating a further breathing parameter comprises at least anticyclic pressure reaction regulation.

20. The method of claim 1, wherein simultaneously regulating a further breathing parameter comprises at least regulation of transition pressure between inspiratory pressure and expiratory pressure.

* * * * *